(12) United States Patent
Silva et al.

(10) Patent No.: US 7,607,433 B2
(45) Date of Patent: *Oct. 27, 2009

(54) GAS DELIVERY AND MONITORING SYSTEM

(75) Inventors: Elizabeth Silva, Houston, TX (US); Ronald Neal Parris, Bellaire, TX (US)

(73) Assignee: Silva-Parris Medical Consultants, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/443,437

(22) Filed: May 31, 2006

(65) Prior Publication Data

US 2006/0278219 A1    Dec. 14, 2006

Related U.S. Application Data

(63) Continuation of application No. 10/922,933, filed on Aug. 23, 2004, now Pat. No. 7,063,085.

(51) Int. Cl.
*A62B 17/04* (2006.01)
*A62B 18/00* (2006.01)

(52) U.S. Cl. .......................... 128/201.24; 128/200.24; 128/201.21; 128/201.22; 128/201.23; 128/202.13; 128/202.16; 128/202.18; 128/202.19; 128/202.27; 128/204.22; 128/205.23; 128/205.26; 128/205.29; 128/206.13; 128/206.23; 128/206.26

(58) Field of Classification Search ............ 128/200.24, 128/201.21, 201.22, 201.23, 201.24, 202.13, 128/202.16, 202.18, 202.19, 202.27, 204.22, 128/205.23, 205.26, 205.29, 206.13, 206.23, 128/206.26

See application file for complete search history.

(56) References Cited

U.S. PATENT DOCUMENTS

| 205,929 | A | 7/1878 | Wallace |
| 1,081,745 | A | 12/1913 | Johnston et al. |
| 1,580,210 | A | 4/1926 | McCulloch |
| 2,047,216 | A | 7/1936 | McKesson |

(Continued)

FOREIGN PATENT DOCUMENTS

JP    2000126016    5/2000

*Primary Examiner*—Patricia M Bianco
*Assistant Examiner*—Nihir Patel
(74) *Attorney, Agent, or Firm*—Morrison and Foerster LLP

(57) ABSTRACT

The present invention provides a system for a gas delivery and monitoring system for delivering a gas product to a patient and receiving a gas product exhaled from a patient. In an embodiment, the gas delivery and monitoring system includes a head support made of resilient material and having therein a facial cavity. The facial cavity is configured to fit the contours of a patient's face and provides an oxygen rich environment for the patient while undergoing a medical procedure. In an embodiment, the facial cavity is shaped substantially in the form of a figure eight. In an embodiment, the facial cavity is further provided with one or more segmented edges that can be removed to further shape the facial cavity to the contours of the patient's face. In an embodiment, tubing is used to deliver oxygen from an oxygen source to the patient. Similarly, tubing is also used to receive carbon dioxide exhaled by the patient so that it might be measured by a carbon dioxide monitor. Still further, an aperture extending from the facial cavity to an outer surface of the head support may be provided as a conduit for the gas products. In yet another embodiment, the tubes may be located within the aperture.

16 Claims, 5 Drawing Sheets

U.S. PATENT DOCUMENTS

| | | |
|---|---|---|
| 2,107,962 A | 2/1938 | Sheasby |
| 2,634,435 A | 4/1953 | Budd |
| 2,688,142 A | 7/1954 | Jensen |
| 2,700,779 A | 2/1955 | Tolkowsky |
| 2,764,153 A | 9/1956 | Stampe |
| 2,940,088 A | 6/1960 | Boos |
| 3,089,153 A | 5/1963 | Bosc |
| 3,140,497 A | 7/1964 | Carswell |
| 3,261,035 A | 7/1966 | Slocum |
| 3,295,521 A | 1/1967 | Balch |
| 3,315,282 A | 4/1967 | Lowery et al. |
| 3,337,883 A | 8/1967 | Allison |
| D214,302 S | 6/1969 | Barber |
| 3,482,571 A | 12/1969 | Behrendt |
| D222,349 S | 10/1971 | Sorenson |
| 3,694,831 A | 10/1972 | Treace |
| 3,926,181 A | 12/1975 | Eischen, Sr. |
| 4,074,376 A | 2/1978 | Bond |
| 4,218,792 A | 8/1980 | Kogan |
| 4,236,264 A | 12/1980 | Britzman |
| 4,259,757 A | 4/1981 | Watson |
| D260,591 S | 9/1981 | Eischen, Sr. |
| 4,349,925 A | 9/1982 | Macomber |
| 4,354,488 A | 10/1982 | Bartos |
| D271,834 S | 12/1983 | Huntsinger |
| D277,059 S | 1/1985 | Boone |
| 4,501,034 A | 2/1985 | Greenawalt |
| 4,504,050 A | 3/1985 | Osborne |
| 4,528,705 A | 7/1985 | Greenawalt |
| 4,550,458 A | 11/1985 | Fiore |
| 4,617,691 A | 10/1986 | Monti et al. |
| 4,752,064 A | 6/1988 | Voss |
| D298,992 S | 12/1988 | Voss |
| 4,826,479 A | 5/1989 | Burgin et al. |
| 5,018,231 A | 5/1991 | Wang |
| 5,216,770 A * | 6/1993 | Holt ............................. 5/639 |
| D337,914 S | 8/1993 | McDonald |
| 5,231,720 A | 8/1993 | Benoff |
| 5,269,035 A | 12/1993 | Hartunian |
| 5,335,656 A | 8/1994 | Bowe |
| 5,387,177 A * | 2/1995 | Dunn ......................... 600/22 |
| 5,426,798 A | 6/1995 | Guarino |
| 5,457,832 A | 10/1995 | Tatum |
| 5,613,501 A | 3/1997 | Michelson |
| D414,974 S | 10/1999 | Marrone et al. |
| 5,960,494 A | 10/1999 | Gilliland et al. |
| 5,970,546 A | 10/1999 | Danis |
| 6,038,720 A | 3/2000 | Matthews et al. |
| 6,088,854 A | 7/2000 | Brownrigg |
| 6,102,040 A | 8/2000 | Tayebi et al. |
| 6,128,797 A | 10/2000 | Shaffer |
| 6,196,223 B1 | 3/2001 | Belfer et al. |
| 6,230,350 B1 | 5/2001 | Goldstein |
| D456,516 S | 4/2002 | Cheshaek et al. |
| 6,374,441 B1 | 4/2002 | Begell |
| 6,412,127 B1 | 7/2002 | Cuddy |
| 6,427,272 B1 | 8/2002 | Yacoub |
| 6,561,194 B2 | 5/2003 | Michelson |
| 6,637,058 B1 | 10/2003 | Lamb |
| 6,668,404 B2 | 12/2003 | Lanteri |
| 6,701,927 B2 | 3/2004 | Kwok et al. |
| 6,745,418 B1 | 6/2004 | Turner, Jr. |
| 6,745,772 B1 | 6/2004 | McLeod |
| 6,842,924 B1 | 1/2005 | Walters |
| 7,063,085 B2 * | 6/2006 | Silva et al. ............. 128/202.18 |
| 2003/0034030 A1 | 2/2003 | Carlucci et al. |

* cited by examiner

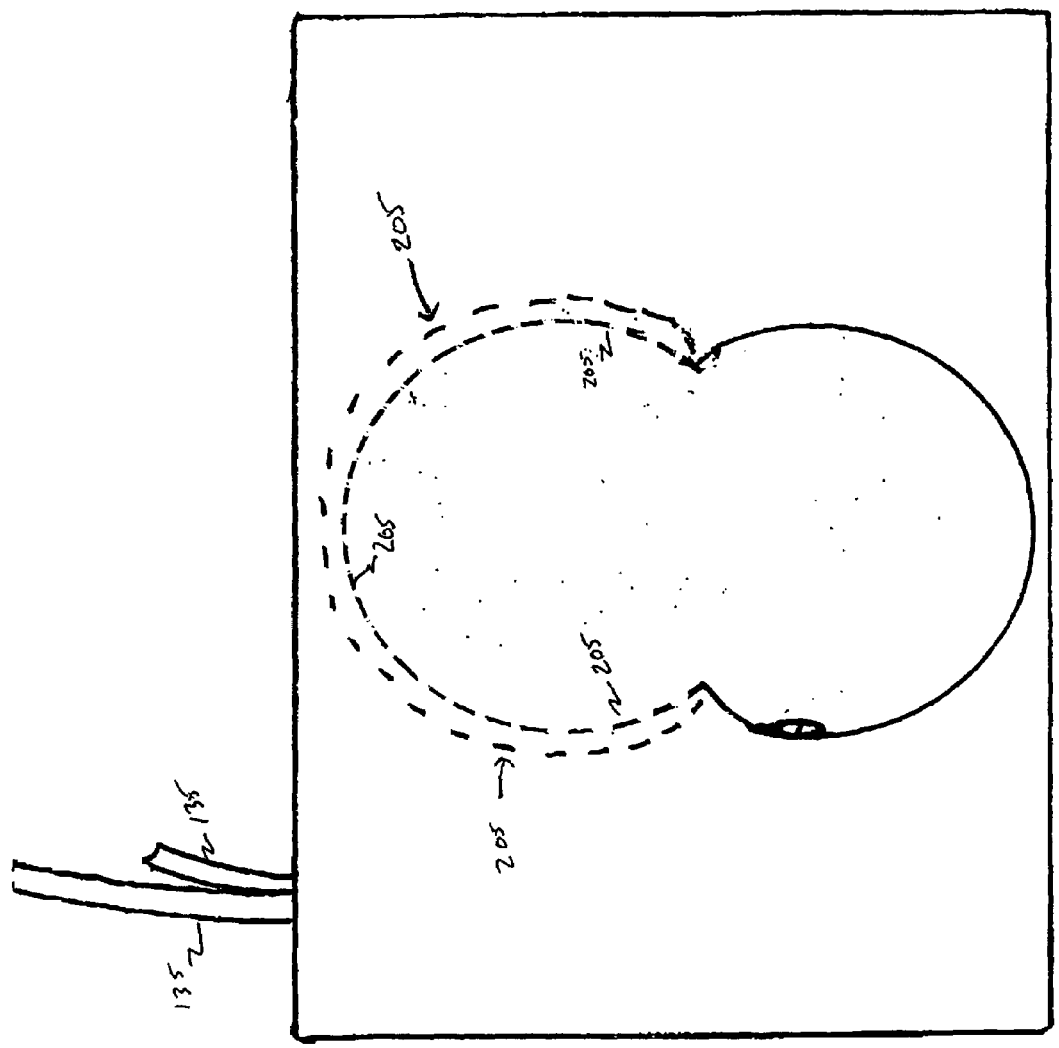

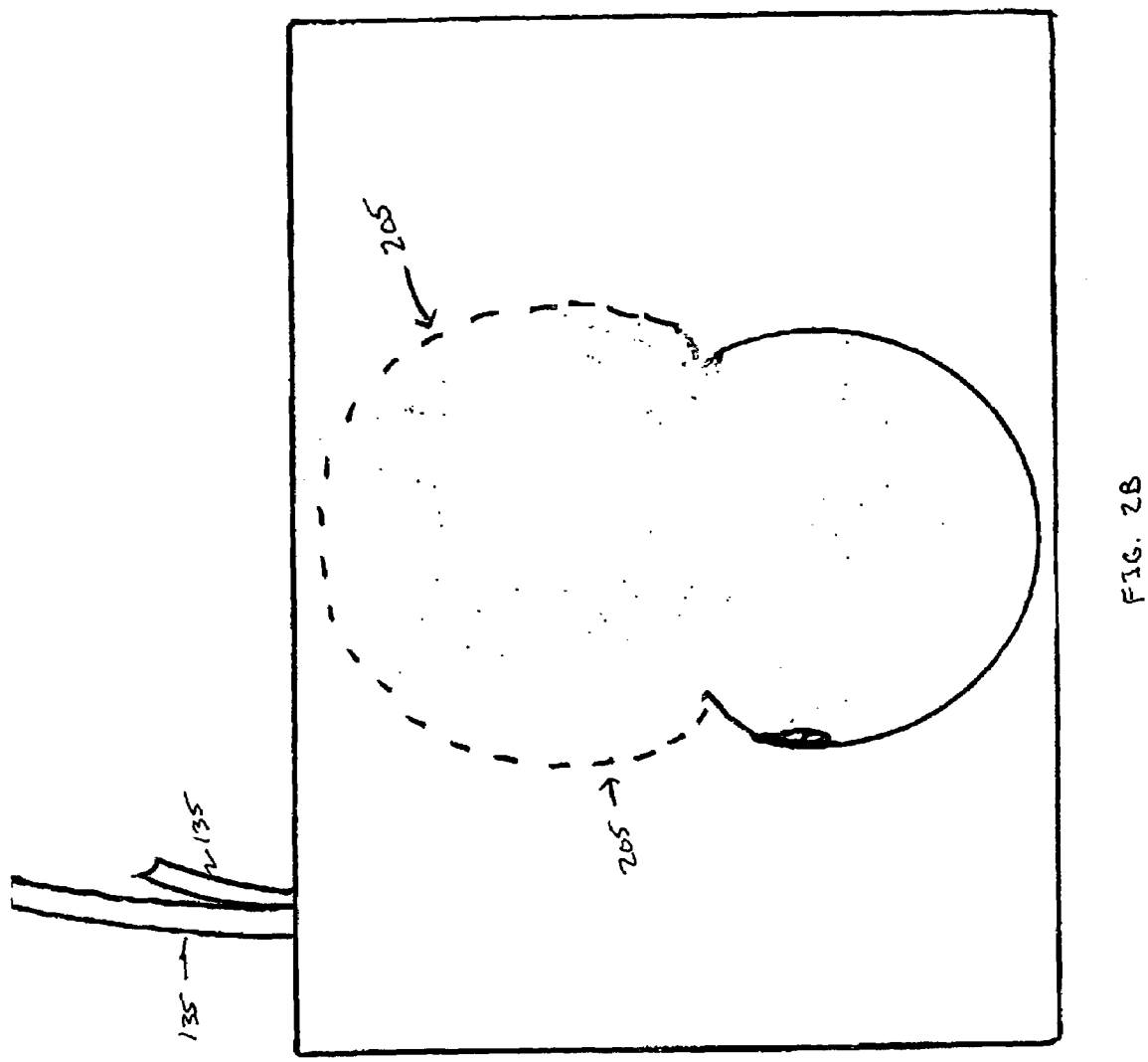

GAS DELIVERY AND MONITORING SYSTEM

CROSS-REFERENCE TO RELATED APPLICATION

This application is a continuation of U.S. Ser. No. 10/922,933, filed Aug. 23, 2004, now U.S. Pat. No. 7,063,085, issued Jun. 20, 2006, the disclosure of which is hereby incorporated by reference.

BACKGROUND OF THE INVENTION

1. Field of Invention

This invention relates to the field of medical devices. More specifically, this invention relates to a system for delivery of gas products to a patient and monitoring of gas products exhaled by the patient.

2. Background

Epidural steroid injections, sacroiliac joint injections, facet joint blocks, and radio frequency ablations are but a few of the wide range of medical procedures being used to help alleviate neck, back, and other joint pain and discomfort. In many of these medical procedures, patients are required to lie face down in a prone position so that a needle can be inserted into the patient's spine. Since the patient is lying face down, a pillow-type support is often used to support the patient's head during the procedure. Some pain is typically associated with the procedures given their invasive nature. Therefore, a patient will often need to be sedated or anesthetized to manage the patient's exposure to such pain. Oxygen delivery and continuous patient monitoring is requisite in the sedated or anesthetized patient. Therefore, in addition to providing comfortable support for the patient's head, the pillow-type support must also provide for unobstructed breathing and patient monitoring.

Current oxygen delivery systems include, but are not limited to, nasal cannulas, face masks, Laryngeal Mask Airways (LMA), and endotracheal tubes (ETT). Selection of the oxygen delivery system is based on the level of sedation, patient position and other individual patient parameters. For the patient in the prone position undergoing a general anesthetic, the standard of care is an endotracheal tube. However, for the prone patient not under general anesthesia, the current oxygen delivery systems all have significant limitations. For example, the ETT or LMA would not be comfortably tolerated by the sedated patient and would therefore not provide an appropriate airway. The nasal cannula and face masks would require that plastic tubing be in contact with the patient's face, thus creating pressure points against the patient's skin and his or her pillow, probably leading to irritation, abrasions, and general discomfort. Still further, not all of these systems allow for monitoring of the patient's expired, end-tidal carbon dioxide ($CO_2$), which is paramount in determining the appropriate safe dose of the sedating medications. Consequently, an end-tidal $CO_2$ siphoning hose must be added to the system to safely monitor the patient. Such hoses are often another source of pressure points against the patient's face.

Another issue that must be taken into consideration is the positioning and support of the prone patient's head and neck. Currently there exists no pillow or headrest specifically designed for the awake, prone patient. A standard pillow is usually employed with the patient's head turned to the side. This position creates uncomfortable pressure points against one side of the patient's face, as well as an unnatural position of the patient's neck. If a face mask is used, there is also a risk that the edge of the mask may migrate into the patient's eyes and cause a corneal abrasion.

Therefore, what is needed is a system for providing an oxygen enriched environment without the need to attach tubing to the patient which can be irritating and cause pressure points.

BRIEF SUMMARY OF THE INVENTION

In accordance with an embodiment of the present invention, a gas delivery and monitoring system is provided for delivering a gas product to a patient and receiving a gas product exhaled from a patient. In an embodiment, a gas delivery and monitoring system comprising a head support made of resilient material and having therein a facial cavity is provided. The facial cavity is configured to fit the contours of a patient's face and provides an oxygen rich environment for the patient while he or she is undergoing medical procedures. Thus in an embodiment, the facial cavity is shaped substantially in the form of a figure eight. In an embodiment, the facial cavity is also provided with one or more segmented edges that can be removed to further shape the facial cavity to the contours of the patient's face. An aperture extending from the facial cavity to an outer surface of the head support may be also be provided and used as a conduit for the gas products. In yet another embodiment, one or more tubes may be located within the aperture. In this case, a first tube may be used to deliver a gas product to a patient and a second tube may be used to receive a gas product exhaled from the patient.

Further features of the present invention, as well as the structure and operation of various embodiments of the present invention are described in detail below with reference to the accompanying drawings.

BRIEF DESCRIPTION OF THE DRAWINGS

The accompanying drawings, which are incorporated herein and form part of the specification, illustrate the present invention and together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

FIGS. 2A and 2B each provide a top perspective view of the segmented edges of the facial cavity in accordance with an embodiment of the present invention.

DETAILED DESCRIPTION OF THE INVENTION

Exemplary System

Figure 1:
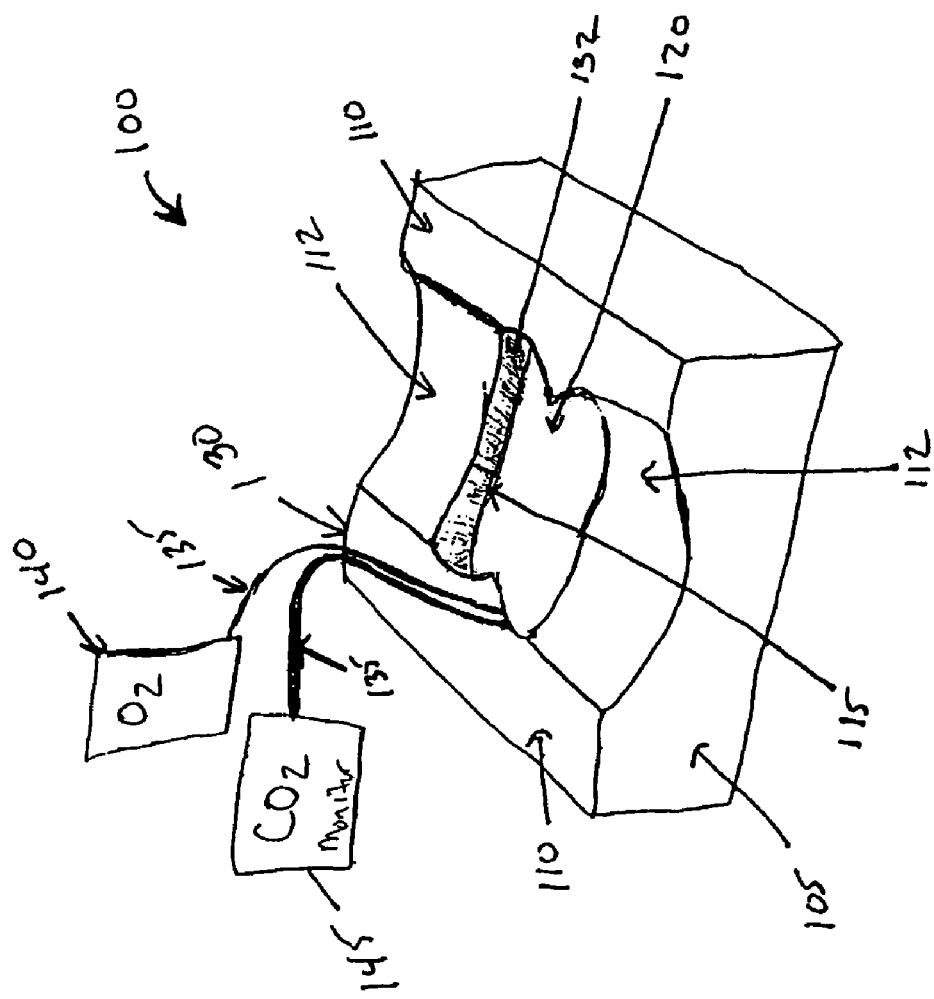
FIG. 1 is a perspective view of a gas delivery system in accordance with an embodiment of the present invention.

Referring to FIG. 1, a gas delivery and monitoring system 100 will now be described in accordance with an embodiment of the present invention. Gas delivery and monitoring system 100 is comprised of a head support 105. In this embodiment, head support 105 includes a top surface 110, a bottom surface 115, outer surfaces 130 and inner surfaces 132. As shown in FIG. 1, head support 105 is substantially rectangular in shape. However, such design is for illustration only and not a limitation. Persons skilled in the relevant art will recognize, based at least on the teachings provided herein, that other variations and shapes may be used without departing from the spirit and scope of the present invention.

Head support 105 may be used to support a patient's head while undergoing procedures which require that the patient lie in the prone position. During such procedures, it is important that the patient's head and neck be maintained in a stable and comfortable position. Thus, in an embodiment, head support 105 is made of a resilient material such as foam or polymeric material like polyurethane or polyethylene which are all capable of being compressed under the weight of a patient's head. In this way, it is possible to avoid placing the patent's head at an uncomfortable height or angle in relation to the patient's neck and spine, thereby avoiding further stress, strain and discomfort. As previously mentioned, oxygen delivery and continuous patient monitoring are extremely important functions in procedures where a patient is sedated or anesthetized. Therefore, head support 105 should not compress under the weight of the patient's head such that the flow of gas is occluded. Given these considerations, the width, length, thickness and overall dimensions of the head support 105 will be apparent to persons skilled in the relevant art. As just mentioned, head support 105 is preferably made of resilient material, thus the top surface 110 will be able to conform somewhat to the contours of each patient's head thereby providing some patient comfort. Still further, in an embodiment, head support 105 may also include one or more concave portions 112 to provide additional contoured support for the forehead and chin of a patient.

In an embodiment, gas delivery and monitoring system 100 is further comprised of a facial cavity 120. Facial cavity 120 extends from the top surface 110 through the bottom surface 115, thereby exposing inner surfaces 132. The facial cavity 120 helps to prevent the creation of pressure points on the patient's face. This avoidance of pressure points is achieved because it is primarily only the patient's forehead and chin which make contact with head support 105. In an embodiment, facial cavity 120 is configured substantially in the shape of a figure eight in order to better match the contours of a patient's face. In this way, the creation of pressure points around the patient's eyes and mouth can be reduced or avoided all together. However, a person skilled in the relevant art will recognize, based at least on the teachings provided herein, that other configurations for the facial cavity 120 may be suitable for minimizing the pressure points on a patient's face.

It is important to realize that the contours of each patient's face varies to some degree. For example, some patients have narrow faces while the faces of others are wide in comparison. Still further, some patient's have high cheek bones as compared to the lower or less prominent cheek bones of others. For this reason, there is a need for a head support that can be adjusted to the contours of each patient's face. Thus, as illustrated in FIG. 2A, facial cavity 120 may also be comprised of segmented edges 205. In an embodiment, segmented edges 205 may be removed to shape the facial cavity 120 more specifically to the contours of a patient's face. In this way, pressure points on the patient's face can be minimized and greater comfort achieved. For example, in FIG. 2B, a number of segmented edges 205 have been removed from the upper and lower portions of facial cavity 120 to accommodate a patient whose face is wide.

Referring again to FIG. 1, in an embodiment, gas delivery and monitoring system 100 also includes one or more tubes 135. Tubes 135 include a distal end and a proximal end. As described herein, distal end refers to the tube ends located furthest away from the facial cavity 120 and proximal end refers to the tube ends located closest to the facial cavity 120. Tubes 135 may be used to deliver gas products to a patient and to receive gas products exhaled from the patient. Thus, in a further embodiment of the present invention, gas delivery and monitoring system 100 may also include a gas delivery source 140 and a gas monitoring source 145. In an embodiment, gas delivery source 140 is used to deliver gas products, such as oxygen, to a patient. However, it will be apparent to persons skilled in the relevant art that gas delivery source 140 could be used to deliver other gas products without departing from the spirit and scope of the present invention. Similarly, gas monitoring source 145 may be used to monitor gas products exhaled by the patient, such as carbon dioxide, for example. In an embodiment, the distal ends of tubes 135 may be attached to gas delivery source 140 and gas monitoring source 145. At the same time, the proximal ends of tubes 135 would be located near the facial cavity 120. In an embodiment, the proximal ends of tubes 135 are flush with an inner surface 132 of head support 120 near the point where a patient's mouth and nose would be located. A first one of tubes 135 could then be used to deliver oxygen to the patient while a second tube 135 could be used for the sampling of end-tidal carbon dioxide exhaled by the patient. In this way, the facial cavity 120 provides an oxygen rich environment in which the patient can breathe comfortably.

Figure 4A:
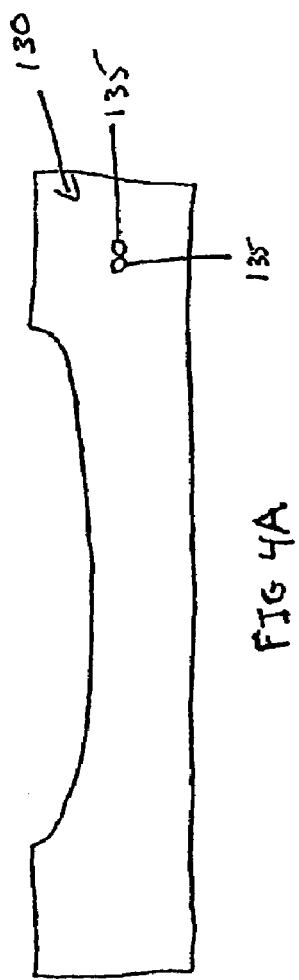
FIGS. 4A, 4B and 4C each provide a side perspective view of a gas delivery system in accordance with embodiments of the present invention.

Head support 105 may be manufactured according to any known process such as injection molding and the like, for example. Referring still to FIG. 1, the head support 105 may be manufactured such that one or more tubes 135 are included with head support 105. Tubes 135 may extend from any one of the top, bottom, or outer surfaces to one of the inner surfaces 132 located within the facial cavity 120. In an embodiment, tubes 135 extend from the outer surface 130 to the inner surface 132 located proximate to where a patient's mouth and nose would be located. In this way, the distal ends of tubes 135 need only be attached to gas delivery source 140 or gas monitoring source 145 when it is time to perform a procedure. FIG. 4A provides a side perspective view of tubes 135 and head support 105.

Figure 3:
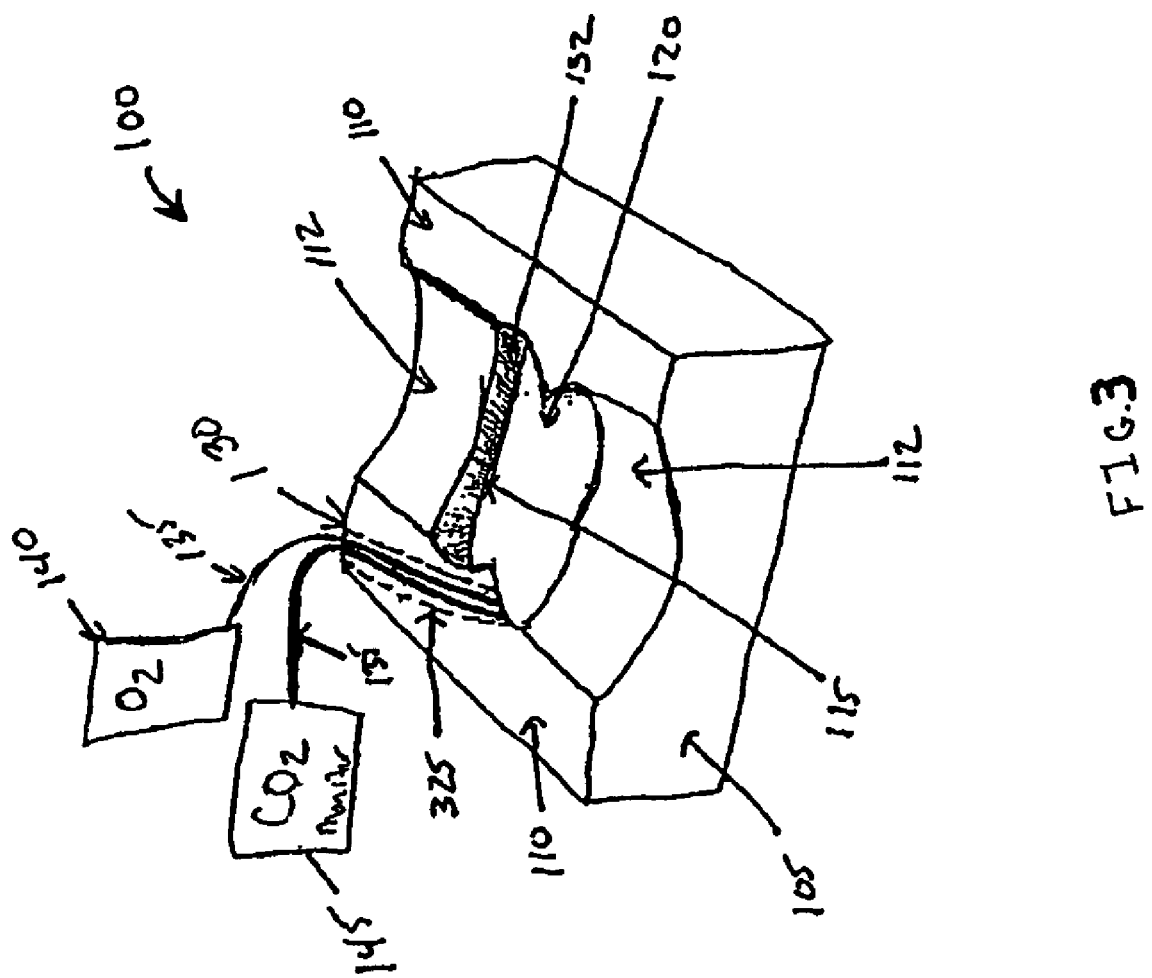
FIG. 3 is a perspective view of a gas delivery system in accordance with an alternative embodiment of the present invention.
Figure 4B:
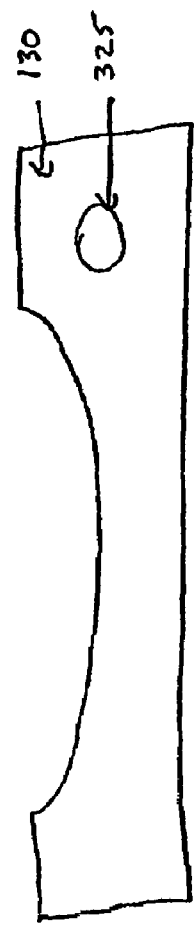
Figure 4C:
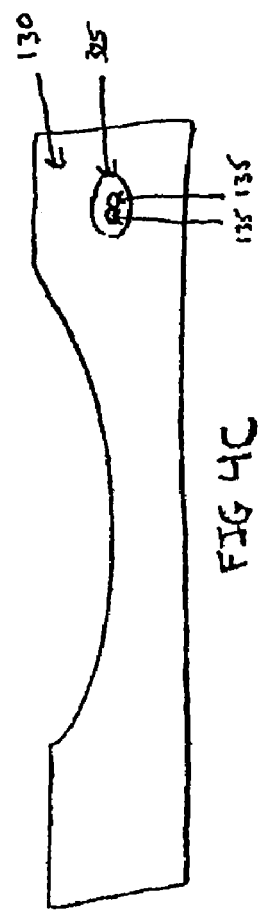

As illustrated in FIG. 3, the head support 105 may be manufactured with an aperture 325. Aperture 325 may extend from any one of the top, bottom, or outer surfaces to one of the inner surfaces 132 located within the facial cavity 120. In an embodiment, aperture 325 extends from the outer surface 130 to the inner surface 132 located proximate to where a patient's mouth and nose would be located. In such an embodiment, aperture 325 may be used as a conduit for the gas products. FIG. 4B provides a side perspective view of aperture 325 and head support 105. Alternatively, one or more tubes 135 may be inserted through the aperture 125 prior to a particular procedure. Tubes 135 may then be used to deliver gas products to the patient or receive gas products exhaled by the patient. In yet another embodiment, tubes 135 and aperture 125 may be included with the head support 105 at the time of manufacture. FIG. 4C provides a side perspective view of aperture 325, tubes 135, and head support 105.

CONCLUSION

While various embodiments of the present invention have been described above, it should be understood that they have been presented by way of example only, and not limitation. It will be understood by those skilled in the relevant art that various changes in form and details may be made therein without departing from the spirit and scope of the invention as defined in the appended claims. Thus, the breadth and scope of the present invention should not be limited by any of the above-described exemplary embodiments, but should only be defined in accordance with the following claims and their equivalents.

What is claimed is:

1. An apparatus, comprising:
a head support configured to support the head of a patient in a prone position,
wherein the head support comprises a facial cavity configured to receive the patient's face; and
a first tube located within the head support to deliver a gas to the patient,
wherein the facial cavity comprises a plurality of removable segments; and
wherein the removable segments are configured to permit adaptation of the facial cavity to the contours of a patient's face by removal of one or more removable segments.

2. The apparatus of claim 1, wherein the first tube is configured to deliver the gas to the patient through the facial cavity.

3. The apparatus of claim 1, further comprising an aperture extending from the facial cavity to an outer surface of the head support.

4. The apparatus of claim 1, further comprising a second tube located within the head support to receive a gas exhaled from the patient.

5. The apparatus of claim 4, wherein the first tube is used to deliver a gas comprising oxygen to the patient and the second tube is used to receive a gas comprising carbon dioxide exhaled from the patient.

6. The apparatus of claim 1, wherein the facial cavity is shaped substantially in the form of a figure-eight.

7. A method of delivering gas to a patient, comprising:
providing a head support configured to support the head of a patient in a prone position,
wherein the head support comprises a facial cavity configured to receive the patient's face; and
wherein the facial cavity comprises a plurality of removable segments;
removing one or more removable segments from said facial cavity of said head support to adapt the facial cavity to the contours of a patient's face;
supporting the head of a patient in a prone position with said head support; and
delivering a gas to the patient through a first tube located within the head support.

8. The method of claim 7, wherein the gas is delivered to the patient through the facial cavity.

9. The method of claim 7, wherein an aperture extends from the facial cavity to an outer surface of the head support.

10. The method of claim 7, further comprising receiving a gas product exhaled from the patient through a second tube located within the head support.

11. The method of claim 10, wherein oxygen is delivered to the patient and the carbon dioxide is received from the patient.

12. The method of claim 7, wherein the facial cavity is shaped substantially in the form of a figure-eight.

13. An apparatus, comprising:
a head support configured to support the head of a patient in a prone position,
wherein the head support comprises a facial cavity configured to receive the patient's face and the facial cavity comprises a plurality of removable segments configured to permit adaptation of the facial cavity to the contours of a patient's face by removal of one or more removable segments;
a first tube located within the head support to deliver a gas to the patient; and
a second tube located within the head support to receive a gas exhaled from the patient.

14. The apparatus of claim 13, wherein the removable segments are configured to permit adaptation of the facial cavity to the contours of a patient's face by removal of one or more removable segments.

15. The apparatus of claim 13, wherein the first tube is used to deliver a gas comprising oxygen to the patient and the second tube is used to receive a gas comprising carbon dioxide exhaled from the patient.

16. The apparatus of claim 13, wherein the facial cavity is shaped substantially in the form of a figure-eight.

* * * * *